(12) United States Patent
Banholzer et al.

(10) Patent No.: US 6,908,928 B2
(45) Date of Patent: Jun. 21, 2005

(54) CRYSTALLINE TIOTROPIUM BROMIDE MONOHYDRATE, PROCESSES FOR THE PREPARATION THEREOF, AND PHARMACEUTICAL COMPOSITIONS

(75) Inventors: Rolf Banholzer, Stuttgart (DE); Peter Sieger, Mittelbiberach (DE); Christian Kulinna, Mainz (DE); Michael Trunk, Ingelheim (DE); Manfred Graulich, Waldalgesheim (DE); Peter Specht, Ober-Hilbersheim (DE); Helmut Meissner, Ingelheim (DE); Andreas Mathes, Ockenheim (DE)

(73) Assignee: BI Pharma KG., Ingelheim (DE)

( * ) Notice: Subject to any disclaimer, the term of this patent is extended or adjusted under 35 U.S.C. 154(b) by 427 days.

(21) Appl. No.: 09/961,822

(22) Filed: Sep. 24, 2001

(65) Prior Publication Data

US 2002/0169321 A1 Nov. 14, 2002

Related U.S. Application Data

(60) Provisional application No. 60/249,349, filed on Nov. 16, 2000.

(30) Foreign Application Priority Data

Oct. 12, 2000 (DE) ......................................... 100 50 621

(51) Int. Cl.[7] ...................... A61K 31/438; C07D 515/18
(52) U.S. Cl. ........................ 514/291; 514/291; 514/304; 546/86; 546/89; 546/91
(58) Field of Search ........................... 546/89, 91, 127; 514/291, 304

(56) References Cited

U.S. PATENT DOCUMENTS

| | | |
|---|---|---|
| 4,042,700 A | 8/1977 | Banholzer et al. |
| 4,783,534 A | 11/1988 | Banholzer |
| 5,610,163 A * | 3/1997 | Banholzer et al. .......... 514/291 |
| 5,654,314 A | 8/1997 | Banholzer et al. |
| 5,770,738 A | 6/1998 | Banholzer et al. |
| 5,952,505 A | 9/1999 | Banholzer |
| 6,486,321 B2 | 11/2002 | Banholzer et al. |
| 6,506,900 B1 | 1/2003 | Banholzer et al. |

FOREIGN PATENT DOCUMENTS

| | | | | |
|---|---|---|---|---|
| EP | 0418716 B1 | 3/1991 | | |
| EP | 0418716 A1 | 3/1991 | | |
| EP | 0418716 B1 * | 4/1994 | | .................. 514/291 |
| SI | 9011744 B * | 9/1990 | | .................. 514/291 |
| WO | WO 9413262 A1 | 6/1994 | | |
| WO | WO 007567 A1 | 2/2000 | | |

OTHER PUBLICATIONS

Accession No. 2002:1138, tiotropium bromide salt, CAS Reg. No. 136310–93–5, derivative of 139404–48–1, tiotropium bromide hydrate, printout of DRUGPAT reference.*
U.S. Patent Application No. 2003/0087927 –Crystalline Anticholinergic, Processes for Preparing it and its use for Preparing a Pharmaceutical Composition published May 8, 2003.
U.S. Patent Application, Crystlline Micronisate, Process for the Manufature thereof and use thereof for the Preparation of a Medicament, accorded Ser. No. 10/385,175, filed Mar. 5, 10, 2003, for Docket No. 1/1310, Bender, H. et al.
U.S. Patent Application HFA Suspension Formulations Containing Anticholinergic accorded Ser. No. 10/392,559 filed Mar. 20, 2003 for Docket No. 1/316, Schmelzer, C.

* cited by examiner

*Primary Examiner*—Alan L. Rotman
*Assistant Examiner*—Janet L Coppins
(74) *Attorney, Agent, or Firm*—Robert P. Raymond; Timothy X. Witkowski; Mary-Ellen Devlin

(57) ABSTRACT

Crystalline monohydrate of $(1\alpha,2\beta,4\beta,5\alpha,7\beta)$-7-[(hydroxydi-2-thienylacetyl)oxy]-9,9-dimethyl-3-oxa-9-azoniatricyclo$[3.3.1.0^{2,4}]$nonane bromide (tiotropium bromide monohydrate), processes for the preparation thereof, pharmaceutical compositions thereof, and their use.

23 Claims, 2 Drawing Sheets

Figure 1:
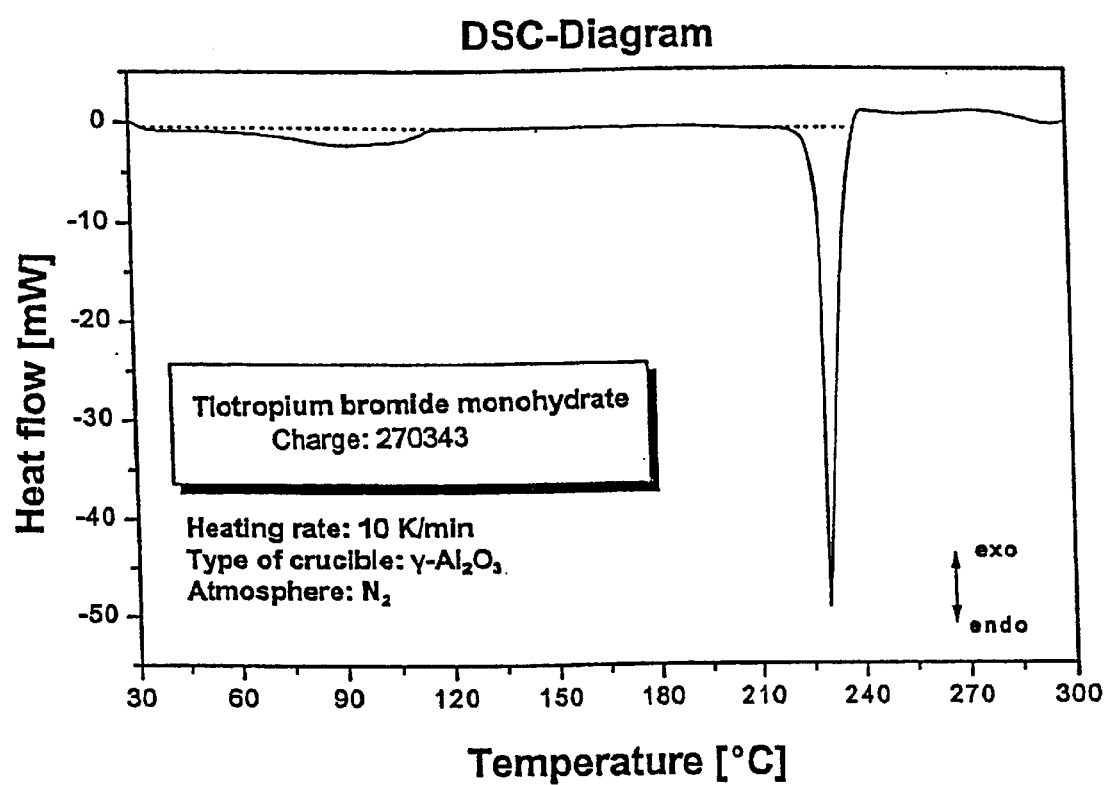

CRYSTALLINE TIOTROPIUM BROMIDE MONOHYDRATE, PROCESSES FOR THE PREPARATION THEREOF, AND PHARMACEUTICAL COMPOSITIONS

RELATED APPLICATIONS

Benefit under 35 U.S.C. §119(e) of prior U.S. provisional application Ser. No. 60/249,349, filed Nov. 16, 2000, is hereby claimed.

BACKGROUND OF THE INVENTION

The invention relates to a crystalline monohydrate of $(1\alpha,2\beta,4\beta,5\alpha,7\beta)$-7-[(hydroxydi-2-thienylacetyl)oxy]-9,9-dimethyl-3-oxa-9-azoniatricyclo[$3.3.1.0^{2,4}$]nonane bromide, processes for the preparation thereof, as well as the use thereof for preparing a pharmaceutical composition, particularly for preparing a pharmaceutical composition having an anticholinergic activity.

The compound $(1\alpha,2\beta,4\beta,5\alpha,7\beta)$-7-[(hydroxydi-2-thienylacetyl)oxy]-9,9-dimethyl-3-oxa-9-azoniatricyclo[$3.3.1.0^{2,4}$]nonane bromide is known from European Patent Application EP 418 716 A1 and has the following chemical structure:

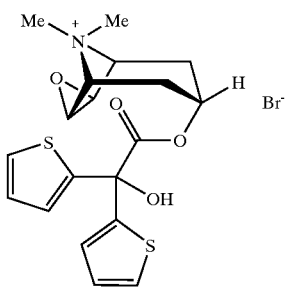

(I)

The compound has valuable pharmacological properties and is known by the name tiotropium bromide (BA679). Tiotropium bromide is a highly effective anticholinergic and can therefore provide therapeutic benefit in the treatment of asthma or chronic obstructive pulmonary disease (COPD).

Tiotropium bromide is preferably administered by inhalation. Suitable inhalable powders packed into appropriate capsules (inhalettes) may be used. Alternatively, it may be administered by the use of suitable inhalable aerosols. These also include powdered inhalable aerosols which contain, for example, HFA134a, HFA227 or mixtures thereof as propellant gas.

The correct manufacture of the abovementioned compositions which are suitable for use for the administration of a pharmaceutically active substance by inhalation is based on various parameters which are connected with the nature of the active substance itself. Without being restrictive, examples of these parameters are the stability of effect of the starting material under various environmental conditions, stability during production of the pharmaceutical formulation and stability in the final medicament compositions. The pharmaceutically active substance used for preparing the abovementioned pharmaceutical compositions should be as pure as possible and its stability in long-term storage must be guaranteed under various environmental conditions. This is absolutely essential to prevent the use of pharmaceutical compositions which contain, in addition to the actual active substance, breakdown products thereof, for example. In such cases the content of active substance in the capsules might be less than that specified.

The absorption of moisture reduces the content of pharmaceutically active substance on account of the weight gain caused by the uptake of water. Pharmaceutical compositions with a tendency to absorb moisture have to be protected from damp during storage, e.g., by the addition of suitable drying agents or by storing the medicament in a damp-proof environment. In addition, the uptake of moisture can reduce the content of pharmaceutically active substance during manufacture if the medicament is exposed to the environment without being protected from damp in any way.

Uniform distribution of the medicament in the formulation is a critical factor, particularly when the medicament has to be given in low doses. To ensure uniform distribution, the particle size of the active substance can be reduced to a suitable level, e.g., by grinding. Another aspect which is important in active substances to be administered by inhalation, e.g., by means of a powder, arises from the fact that only particles of a certain size can be taken into the lungs by inhalation. The particle size of these lung-bound particles (inhalable fraction) is in the sub-micron range. In order to obtain active substances of a corresponding particle size, a grinding process (so-called micronizing) is again required.

Since breakdown of the pharmaceutically active substance as a side effect of the grinding (or micronizing) has to be avoided as far as possible, in spite of the hard conditions required during the process, it is absolutely essential that the active substance should be highly stable throughout the grinding process. Only if the active substance is sufficiently stable during the grinding process is it possible to produce a homogeneous pharmaceutical formulation which always contains the specified amount of active substance in reproducible manner.

Another problem which may arise in the grinding process for preparing the desired pharmaceutical formulation is the input of energy caused by this process and the stress on the surface of the crystals. This may in certain circumstances lead to polymorphous changes, to a change in the amorphous configuration or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a new, stable crystalline form of the compound tiotropium bromide which meets the stringent requirements imposed on pharmaceutically active substances as mentioned above.

DETAILED DESCRIPTION OF THE INVENTION

It has been found that, depending on the choice of conditions which can be used when purifying the crude product obtained after industrial manufacture, tiotropium bromide occurs in various crystalline modifications.

It has been found that these different modifications can be deliberately produced by selecting the solvents used for the crystallization as well as by a suitable choice of the process conditions used in the crystallization process.

Surprisingly, it has been found that the monohydrate of tiotropium bromide, which can be obtained in crystalline form by choosing specific reaction conditions, meets the stringent requirements mentioned above and thus solves the problem on which the present invention is based. Accordingly the present invention relates to crystalline tiotropium bromide monohydrate.

According to another aspect, the present invention relates to a process for preparing crystalline hydrates of tiotropium bromide. This preparation process is characterized in that tiotropium bromide, which has been obtained for example by the method disclosed in EP 418 716 A1, is taken up in water, the mixture obtained is heated and finally the hydrates of tiotropium bromide are crystallized while cooling slowly.

The present invention further relates to crystalline hydrates of tiotropium bromide which may be obtained by the above method.

One aspect of the present invention relates to a process for preparing crystalline tiotropium bromide monohydrate which is described in more detail hereinafter.

In order to prepare the crystalline monohydrate according to the present invention, tiotropium bromide, which has been obtained for example according to the method disclosed in EP 418 716 A1, has to be taken up in water and heated, then purified with activated charcoal and, after removal of the activated charcoal, the tiotropium bromide monohydrate has to be crystallized out slowly while cooling gently.

The method described below is preferably used according to the invention.

In a suitably dimensioned reaction vessel the solvent is mixed with tiotropium bromide, which has been obtained, for example, according to the method disclosed in EP 418 716 A1. 0.4 kg to 1.5 kg, preferably 0.6 kg to 1 kg, most preferably about 0.8 kg of water are used as solvent per mole of tiotropium bromide used. The mixture obtained is heated with stirring, preferably to more than 50° C., most preferably to more than 60° C. The maximum temperature which can be selected will be determined by the boiling point of the solvent used, i.e., water. Preferably the mixture is heated to a range from 80° C.–90° C.

Activated charcoal, dry or moistened with water, is added to this solution. 10 g to 50 g, more preferably 15 g to 35 g, most preferably about 25 g of activated charcoal are put in per mole of tiotropium bromide used. If desired, the activated charcoal is suspended in water before being added to the solution containing the tiotropium bromide. 70 g to 200 g, preferably 100 g to 160 g, most preferably about 135 g water are used to suspend the activated charcoal, per mole of tiotropium bromide used. If the activated charcoal is suspended in water prior to being added to the solution containing the tiotropium bromide, it is advisable to rinse with the same amount of water.

After the activated charcoal has been added, stirring is continued at constant temperature for between 5 and 60 minutes, preferably between 10 and 30 minutes, most preferably about 15 minutes, and the mixture obtained is filtered to remove the activated charcoal. The filter is then rinsed with water. 140 g to 400 g, preferably 200 g to 320 g, most preferably about 270 g of water are used for this, per mole of tiotropium bromide used.

The filtrate is then slowly cooled, preferably to a temperature of 20° C.–25° C. The cooling is preferably carried out at a cooling rate of 1° C. to 10° C. per 10 to 30 minutes, preferably 2° C. to 8° C. per 10 to 30 minutes, more preferably 3° C. to 5° C. per 10 to 20 minutes, most preferably 3° C. to 5° C. roughly per 20 minutes. If desired, the cooling to 20° C. to 25° C. may be followed by further cooling to below 20° C., most preferably to 10° C. to 15° C.

Once the filtrate has cooled, it is stirred for between 20 minutes and 3 hours, preferably between 40 minutes and 2 hours, most preferably about one hour, to complete the crystallization.

The crystals formed are finally isolated by filtering or suction filtering the solvent. If it proves necessary to subject the crystals obtained to another washing step, it is advisable to use water or acetone as the washing solvent. 0.1 l to 1.0 l, preferably 0.2 l to 0.5 l, most preferably about 0.3 l solvent are used, per mole of tiotropium bromide, to wash the tiotropium bromide monohydrate crystals obtained. If desired the washing step may be repeated.

The product obtained is dried in vacuo or using circulating hot air until a water content of 2.5%–4.0% is obtained.

One aspect of the present invention relates to crystalline tiotropium bromide monohydrate which can be obtained using the method described above.

The tiotropium bromide monohydrate obtainable using the method described above was investigated by Differential Scanning Calorimetry (DSC). The DSC diagram shows two characteristic signals. The first, relatively broad, endothermic signal between 50–120° C. can be attributed to the dehydration of the tiotropium bromide monohydrate into the anhydrous form. The second, relatively sharp, endothermic peak at 230° C.±5° C. can be put down to the melting of the substance (FIG. 1). This data was obtained using a Mettler DSC 821 and evaluated using the Mettler STAR software package. The data was recorded at a heating rate of 10 K/min.

Since the substance melts with decomposition (i.e., incongruent melting process), the melting point observed depends to a great extent on the heating rate. At lower heating rates, the melting/decomposition process is observed at significantly lower temperatures, e.g., at 220° C. ±5° C. with a heating rate of 3 K/min. It is also possible that the melting peak may be split. The split is all the more apparent the lower the heating rate in the DSC experiment.

The present invention is therefore directed to crystalline tiotropium bromide monohydrate which is characterized, according to FIG. 1, by an endothermic peak at 230° C. (±5° C.) at a heating rate of 10 K/min.

Figure 2:
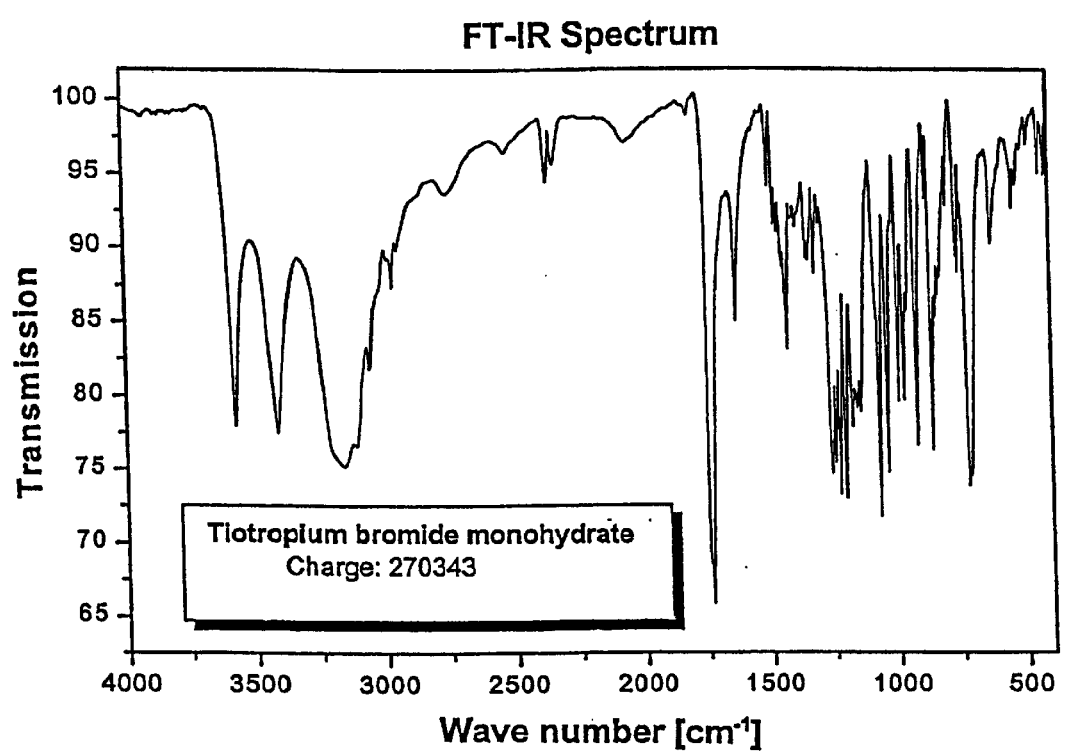

The tiotropium bromide monohydrate according to the invention was characterized by IR spectroscopy. The data was obtained using a Nicolet FTIR spectrometer and evaluated with the Nicolet OMNIC software package, version 3.1. The measurement was carried out with 2.5 μmol of tiotropium bromide monohydrate in 300 mg of KBr. The IR spectrum obtained is shown in FIG. 2. Table 1 shows some of the essential bands of the IR spectrum.

TABLE 1

Attribution of Specific Bands

| Wave number (cm$^{-1}$) | Attribution | Type of Oscillation |
| --- | --- | --- |
| 3570, 410 | O—H | elongated oscillation |
| 3105 | Aryl C—H | elongated oscillation |
| 1730 | C=0 | elongated oscillation |
| 1260 | Epoxide C—O | elongated oscillation |
| 1035 | Ester C—OC | elongated oscillation |
| 720 | Thiophene | cyclic oscillation |

Accordingly, the present invention relates to crystalline tiotropium bromide monohydrate which is characterized according to FIG. 2 by an IR spectrum which has bands at wave numbers 3570, 3410, 3105, 1730, 1260, 1035 and 720 cm$^{-1}$, inter alia.

The tiotropium bromide monohydrate according to the invention was characterized by X-ray structural analysis. The measurements of X-ray diffraction intensity were carried out on an AFC7R-4-circuit diffractometer (Rigaku) using monochromatic copper $K_\alpha$ radiation. The structural solution and refinement of the crystal structure were obtained by direct methods (SHELXS86 Program) and FMLQ-refinement (TeXsan Program). Experimental details of the crystalline structural resolution and refinement are collected in Table 2.

TABLE 2

Experimental Data on the Analysis of the Crystalline Structure of Tiotropium Bromide Monohydrate

A. CRYSTAL DATA

| | |
|---|---|
| Empirical Formula | [C$_{19}$H$_{22}$NO$_4$S$_2$]Br.H$_2$O |
| Formula Weight | 472.43 + 18.00 |
| Color and shape of crystals | colorless, prismatic |
| Dimensions of crystals | 0.2 × 0.3 × 0.3 mm |
| Crystal system | monoclinic |
| Lattice type | primitive |
| Space group | P 2$_1$/n |
| Lattice constants | a = 18.0774 Å |
| | b = 11.9711 Å |
| | c = 9.9321 Å |
| | β = 102.691° |
| | V = 2096.96 Å$^3$ |
| Formula units per elementary cell | 4 |

B. MEASUREMENTS OF INTENSITY

| | |
|---|---|
| Diffractometer | Rigaku AFC7R |
| X-ray generator | Rigaku RU200 |
| Wavelength | λ = 1.54178 Å (monochromatic copper $K_\alpha$-radiation) |
| Current, voltage | 50 kV, 100 mA |
| Take-off angle | 6° C. |
| Crystal assembly | steam-saturated capillary |
| Crystal-detector gap | 235 mm |
| Detector opening | 3.0 mm vertical and horizontal |
| Temperature | 18° C. |
| Determining the lattice constants | 25 reflexes (50.8° < 2Θ < 56.2°) |
| Scan type | ω-2Θ |
| Scan speed | 8.0 32.0°/min in ω |
| Scan width | (0.58 + 0.30 tan Θ)° |
| 2Θ$_{max}$ | 120° |
| Measured | 5193 |
| Independent reflexes | 3281 (R$_{int}$ = 0.051) |
| Corrections | Lorentz polarization |
| | Absorption |
| | (Transmission factors 0.56–1.00) |
| | Crystal decay: 10.47% decay |

C. REFINEMENT

| | |
|---|---|
| Reflections (I > 3σI) | 1978 |
| Variable | 254 |
| Ratio of reflections/parameters | 7.8 |
| R-values: R, Rw | 0.062, 0.066 |

The X-ray structural analysis carried out showed that crystalline tiotropium bromide hydrate has a simple monoclinic cell with the following dimensions: a=18.0774 Å, b=11.9711 Å, c=9.9321 Å, β=102.691°, V=2096.96 Å$^3$. Accordingly, the present invention relates to crystalline tiotropium bromide monohydrate which is characterized by the elementary cell described above.

The atomic coordinates described in Table 3 were determined by the above X-ray structural analysis.

TABLE 3

Coordinates

| Atom | x | y | z | u (eq) |
|---|---|---|---|---|
| Br(1) | 0.63938(7) | 0.0490(1) | 0.2651(1) | 0.0696(4) |
| S(1) | 0.2807(2) | 0.8774(3) | 0.1219(3) | 0.086(1) |
| S(2) | 0.4555(3) | 0.6370(4) | 0.4214(5) | 0.141(2) |
| O(1) | 0.2185(4) | 0.7372(6) | 0.4365(8) | 0.079(3) |
| O(2) | 0.3162(4) | 0.6363(8) | 0.5349(9) | 0.106(3) |
| O(3) | 0.3188(4) | 0.9012(5) | 0.4097(6) | 0.058(2) |
| O(4) | 0.0416(4) | 0.9429(6) | 0.3390(8) | 0.085(3) |
| O(5) | 0.8185(5) | 0.0004(8) | 0.2629(9) | 0.106(3) |
| N(1) | 0.0111(4) | 0.7607(6) | 0.4752(7) | 0.052(2) |
| C(1) | 0.2895(5) | 0.7107(9) | 0.4632(9) | 0.048(3) |
| C(2) | 0.3330(5) | 0.7876(8) | 0.3826(8) | 0.048(3) |
| C(3) | 0.3004(5) | 0.7672(8) | 0.2296(8) | 0.046(3) |
| C(4) | 0.4173(5) | 0.7650(8) | 0.4148(8) | 0.052(3) |
| C(5) | 0.1635(5) | 0.6746(9) | 0.497(1) | 0.062(3) |
| C(6) | 0.1435(5) | 0.7488(9) | 0.6085(9) | 0.057(3) |
| C(7) | 0.0989(6) | 0.6415(8) | 0.378(1) | 0.059(3) |
| C(8) | 0.0382(5) | 0.7325(9) | 0.3439(9) | 0.056(3) |
| C(9) | 0.0761(6) | 0.840(1) | 0.315(1) | 0.064(3) |
| C(10) | 0.1014(6) | 0.8974(8) | 0.443(1) | 0.060(3) |
| C(11) | 0.0785(5) | 0.8286(8) | 0.5540(9) | 0.053(3) |
| C(12) | −0.0632(6) | 0.826(1) | 0.444(1) | 0.086(4) |
| C(13) | −0.0063(6) | 0.6595(9) | 0.554(1) | 0.062(3) |
| C(14) | 0.4747(4) | 0.8652(9) | 0.430(1) | 0.030(2) |
| C(15) | 0.2839(5) | 0.6644(9) | 0.1629(9) | 0.055(3) |
| C(16) | 0.528(2) | 0.818(2) | 0.445(2) | 0.22(1) |
| C(17) | 0.5445(5) | 0.702(2) | 0.441(1) | 0.144(6) |
| C(18) | 0.2552(6) | 0.684(1) | 0.019(1) | 0.079(4) |
| C(19) | 0.2507(6) | 0.792(1) | −0.016(1) | 0.080(4) |
| H(1) | −0.0767 | 0.8453 | 0.5286 | 0.102 |
| H(2) | −0.0572 | 0.8919 | 0.3949 | 0.102 |
| H(3) | −0.1021 | 0.7810 | 0.3906 | 0.102 |
| H(4) | −0.0210 | 0.6826 | 0.6359 | 0.073 |
| H(5) | −0.0463 | 0.6178 | 0.4982 | 0.073 |
| H(6) | 0.0377 | 0.6134 | 0.5781 | 0.073 |
| H(7) | 0.1300 | 0.7026 | 0.6770 | 0.069 |
| H(8) | 0.1873 | 0.7915 | 0.6490 | 0.069 |
| H(9) | 0.1190 | 0.6284 | 0.2985 | 0.069 |
| H(10) | 0.0762 | 0.5750 | 0.4016 | 0.069 |
| H(11) | 0.1873 | 0.6082 | 0.5393 | 0.073 |
| H(12) | −0.0025 | 0.7116 | 0.2699 | 0.066 |
| H(13) | 0.1084 | 0.8383 | 0.2506 | 0.075 |
| H(14) | 0.1498 | 0.9329 | 0.4626 | 0.071 |
| H(15) | 0.0658 | 0.8734 | 0.6250 | 0.063 |
| H(16) | 0.2906 | 0.5927 | 0.2065 | 0.065 |
| H(17) | 0.2406 | 0.6258 | −0.0469 | 0.094 |
| H(18) | 0.2328 | 0.8191 | −0.1075 | 0.097 |
| H(19) | 0.4649 | 0.9443 | 0.4254 | 0.037 |
| H(20) | 0.5729 | 0.8656 | 0.4660 | 0.268 |
| H(21) | 0.5930 | 0.6651 | 0.4477 | 0.165 |
| H(22) | 0.8192 | −0.0610 | 0.1619 | 0.084 |
| H(23) | 0.7603 | 0.0105 | 0.2412 | 0.084 | x, y, z: fractional coordinates; and
u (eq): mean quadratic amplitude of atomic movement in the crystal According to another aspect, the present invention relates to the use of tiotropium bromide monohydrate as a medicament in the light of the pharmaceutical efficacy of the hydrate according to the invention.

To prepare a medicament which can be inhaled, particularly an inhalable powder, which contains the crystalline tiotropium bromide monohydrate described by the present invention, methods known from the prior art may be used. In this respect, reference is made, for example, to the teaching of DE-A-179 22 07. Accordingly, a further aspect of the present invention relates to inhalable powders characterized in that they contain tiotropium bromide monohydrate.

In view of the anticholinergic effects of tiotropium bromide monohydrate a further aspect of the present invention relates to the use of tiotropium bromide monohydrate for preparing a pharmaceutical composition for treating diseases in which the use of an anticholinergic agent may have a therapeutic benefit. It is preferably used for preparing a pharmaceutical composition for treating asthma or COPD.

The following example of synthesis serves to illustrate a method of preparing crystalline tiotropium bromide monohydrate carried out by way of example. It is to be regarded only as a possible method described by way of example, without restricting the invention to its contents.

Example of Synthesis

In a suitable reaction vessel, 15.0 kg of tiotropium bromide are added to 25.7 kg of water. The mixture is heated to 80° C.–90° C. and stirred at constant temperature until a clear solution is formed. Activated charcoal (0.8 kg), moistened with water, is suspended in 4.4 kg of water, this mixture is added to the solution containing the tiotropium bromide and rinsed with 4.3 kg of water. The mixture thus obtained is stirred for at least 15 minutes at 80° C.–90° C. and then filtered through a heated filter into an apparatus which has been preheated to an outer temperature of 70° C. The filter is rinsed with 8.6 kg of water. The contents of the apparatus are cooled to a temperature of 20° C.–25° C. at a rate of 3° C.–5° C. per 20 minutes. The apparatus is further cooled to 10° C.–15° C. using cold water, and the crystallization is completed by stirring for at least one hour. The crystals are isolated using a suction filter drier, the crystal slurry isolated is washed with 9 l of cold water (10° C.–15° C.) and cold acetone (10° C.–15° C.). The crystals obtained are dried at 25° C. for 2 hours in a nitrogen current. Yield: 13.4 kg of tiotropium bromide monohydrate (86% of theory).

We claim:

1. A pharmaceutical composition comprising:
   (a) an effective amount of crystalline tiotropium bromide monohydrate having an endothermic peak at 230° C.±5° C. occurring during thermal analysis using DSC at a heating rate of 10 K/mm; and
   (b) a pharmaceutically acceptable excipient.

2. A pharmaceutical composition comprising:
   (a) an effective amount of crystalline tiotropium bromide monohydrate having an JR spectrum comprising bands at wave numbers 3570, 3410, 3105, 1730, 1260, 1035, and 720 cm$^{-1}$; and
   (b) a pharmaceutically acceptable excipient.

3. A pharmaceutical composition comprising:
   (a) an effective amount of crystalline tiotropium bromide monohydrate having (i) an endothermic peak at 230° C.±5° C. occurring during thermal analysis using DSC at a heating rate of 10 K/mm, and (ii) an JR spectrum comprising bands at wave numbers 3570, 3410, 3105, 1730, 1260, 1035, and 720 cm$^{-1}$; and
   (b) a pharmaceutically acceptable excipient.

4. A pharmaceutical composition comprising:
   (a) an effective amount of crystalline tiotropium bromide monohydrate having a single monoclinic cell having the following dimensions: a=18.0774 Å, b=11.9711 Å, c=9.9321 Å, β=102.691°, and V=2096.96 Å$^3$; and
   (b) a pharmaceutically acceptable excipient.

5. A pharmaceutical composition comprising:
   (a) an effective amount of crystalline tiotropium bromide monohydrate having (i) an endothermic peak at 230° C.±5° C. occurring during thermal analysis using DSC at a heating rate of 10 K/mm, and (ii) a single monoclinic cell having the following dimensions: a=18.0774 Å, b=11.9711 Å, c=9.9321 Å, β=102.691°, and V=2096.96 Å$^3$; and
   (b) a pharmaceutically acceptable excipient.

6. A pharmaceutical composition comprising:
   (a) an effective amount of crystalline tiotropium bromide monohydrate having (i) an IR spectrum comprising bands at wave numbers 3570, 3410, 3105, 1730, 1260, 1035, and 720 cm$^{-1}$, and (ii) a single monoclinic cell having the following dimensions: a=18.0774 Å, b=11.9711 Å, c=9.9321 Å, β=102.691°, and V=2096.96 Å$^3$; and
   (b) a pharmaceutically acceptable excipient.

7. A pharmaceutical composition comprising:
   (a) an effective amount of crystalline tiotropium bromide monohydrate having (i) an endothermic peak at 230° C.±5° C. occurring during thermal analysis using DSC at a heating rate of 10 K/min, (ii) an JR spectrum comprising bands at wave numbers 3570, 3410, 3105, 1730, 1260, 1035, and 720 cm$^{-1}$, and (iii) a single monoclinic cell having the following dimensions: a=18.0774 Å, b=11.9711 Å, c=9.9321 Å, 13.102.691°, and V=2096.96 |$^3$; and
   (b) a pharmaceutically acceptable excipient.

8. The pharmaceutical composition according to claim 1, wherein the pharmaceutical composition is an inhalable powder.

9. The pharmaceutical composition according to claim 2, wherein the pharmaceutical composition is an inhalable powder.

10. The pharmaceutical composition according to claim 3, wherein the pharmaceutical composition is an inhalable powder.

11. The pharmaceutical composition according to claim 4, wherein the pharmaceutical composition is an inhalable powder.

12. The pharmaceutical composition according to claim 5, wherein the pharmaceutical composition is an inhalable powder.

13. The pharmaceutical composition according to claim 6, wherein the pharmaceutical composition is an inhalable powder.

14. The pharmaceutical composition according to claim 7, wherein the pharmaceutical composition is an inhalable powder.

15. A method for treatment of diseases in which the administration of an anticholinergic agent may have a therapeutic benefit, in a patient in need of such treatment, which method comprises administering the patient an effective amount of crystalline tiotropium bromide monohydrate having an endothermic peak at 230° C.±5° C. occurring during thermal analysis using DSC at a heating rate of 10 K/mm.

16. A method for treatment of diseases in which the administration of an anticholinergic agent may have a therapeutic benefit, in a patient in need of such treatment, which method comprises administering the patient an effective amount of crystalline tiotropium bromide monohydrate having an JR spectrum comprising bands at wave numbers 3570, 3410, 3105, 1730, 1260, 1035, and 720 cm$^{-1}$.

17. A method for treatment of diseases in which the administration of an anticholinergic agent may have a therapeutic benefit, in a patient in need of such treatment, which method comprises administering the patient an effective amount of crystalline tiotropium bromide monohydrate having (i) an endothermic peak at 230° C.±5° C. occurring during thermal analysis using DSC at a heating rate of 10 K/min, and (ii) an JR spectrum comprising bands at wave numbers 3570, 3410, 3105, 1730, 1260, 1035, and 720 cm$^{-1}$.

18. A method for treatment of diseases in which the administration of an anticholinergic agent may have a therapeutic benefit, in a patient in need of such treatment, which method comprises administering the patient an effective amount of crystalline tiotropium bromide monohydrate having a single monoclinic cell having the following dimensions: a=18.0774 Å, b=11.9711 Å, c=9.9321 Å, β=102.6910, and V=2096.96 Å$^3$.

19. Crystalline hydrates of tiotropium bromide obtained by a process comprising:
(a) dissolving tiotropium bromide in water to obtain a solution;
(b) heating the solution of step (a);
(c) adding activated charcoal to the heated solution of step (b);
(d) removing the activated charcoal from the solution of step (c); and
(e) allowing the solution to slowly cool to obtain crystalline hydrates of tiotropium bromide.

20. Crystalline hydrates of tiotropium bromide according to claim 19, wherein the solution of step (a) is heated to more than 50° C.

21. A method for treatment of diseases in which the administration of an anticholinergic agent may have a therapeutic benefit, in a patient in need of such treatment, which method comprises administering the patient an effective amount of crystalline tiotropium bromide monohydrate having (i) an endothermic peak at 230° C.±5° C. occurring during thermal analysis using DSC at a heating rate of 10 K/mm, and (ii) a single monoclinic cell having the following dimensions: a=18.0774 Å, b=11.9711 Å, c=9.9321 Å, β=102.691°, and V=2096.96 |$^3$.

22. A method for treatment of diseases in which the administration of an anticholinergic agent may have a therapeutic benefit, in a patient in need of such treatment, which method comprises administering the patient an effective amount of crystalline tiotropium bromide monohydrate having (i) an IR spectrum comprising bands at wave numbers 3570, 3410, 3105, 1730, 1260, 1035, and 720 cm$^{-1}$, and (ii) a single monoclinic cell having the following dimensions: a=18.0774 Å, b=11.9711 Å, c=9.9321 Å, β=102.691°, and V=2096.96 Å$^3$.

23. A method for treatment of diseases in which the administration of an anticholinergic agent may have a therapeutic benefit, in a patient in need of such treatment, which method comprises administering the patient an effective amount of crystalline tiotropium bromide monohydrate having (i) an endothermic peak at 230° C. ±5° C. occurring during thermal analysis using DSC at a heating rate of 10 K/mm, (ii) an IR spectrum comprising bands at wave numbers 3570, 3410, 3105, 1730, 1260, 1035, and 720 cm$^{-1}$, and (iii) a single monoclinic cell having the following dimensions: a=18.0774 Å, b=11.9711 Å, c=9.9321 Å, β=102.691°, and V=2096.96 Å$^3$.

* * * * *

UNITED STATES PATENT AND TRADEMARK OFFICE
CERTIFICATE OF CORRECTION

PATENT NO.        : 6,908,928 B2
APPLICATION NO. : 09/961822
DATED             : June 21, 2005
INVENTOR(S)       : Banholzer et al.

It is certified that error appears in the above-identified patent and that said Letters Patent is hereby corrected as shown below:

In Column 7, line 41 (Claim 2):
"JR spectrum" should read
--IR spectrum--

In Column 7, line 49 (Claim 3):
"JR spectrum" should read
--IR spectrum--

In Column 8, line 15 (Claim 7):
"JR spectrum" should read
--IR spectrum--

In Column 8, line 19 (Claim 7):
"13.102.691°" should read
--$\beta = 102.691°$--

In Column 8, line 20 (Claim 7):
"V=2096.96 |³" should read
--$V = 2096.96 \text{ Å}^3$--

In Column 8, line 43 (Claim 15):
"A method for treatment of diseases in which the administration...." should read
--A method for treatment of the diseases asthma or COPD in which the administration....--

In Column 8, line 49 (Claim 15):
"K/mm." should read
--K/min.--

In Column 8, line 50 (Claim 16):
"A method for treatment of diseases in which the administration...." should read
--A method for treatment of the diseases asthma or COPD in which the administration....--

UNITED STATES PATENT AND TRADEMARK OFFICE
CERTIFICATE OF CORRECTION

PATENT NO. : 6,908,928 B2
APPLICATION NO. : 09/961822
DATED : June 21, 2005
INVENTOR(S) : Banholzer et al.

It is certified that error appears in the above-identified patent and that said Letters Patent is hereby corrected as shown below:

In Column 8, line 55 (Claim 16):
"JR spectrum" should read
--IR spectrum--

In Column 8, line 57 (Claim 17):
"A method for treatment of diseases in which the administration...." should read
--A method for treatment of the diseases asthma or COPD in which the administration....--

In Column 8, line 64 (Claim 17):
"JR spectrum" should read
--IR spectrum--

In Column 8, line 66 (Claim 18):
"A method for treatment of diseases in which the administration...." should read
--A method for treatment of the diseases asthma or COPD in which the administration....--

In Column 9, line 5 (Claim 18):
"$\beta=102.6910$" should read
--$\beta=102.691°$--

In Column 9, line 22 (Claim 21):
"A method for treatment of diseases in which the administration...." should read
--A method for treatment of the diseases asthma or COPD in which the administration....--

In Column 10, line 1 (Claim 21):
"K/mm" should read
--K/min--

In Column 10, line 3 (Claim 21):
"$V=2096.96 \mid ^3$" should read
--$V=2096.96 \text{ Å}^3$--

UNITED STATES PATENT AND TRADEMARK OFFICE
CERTIFICATE OF CORRECTION

PATENT NO. : 6,908,928 B2
APPLICATION NO. : 09/961822
DATED : June 21, 2005
INVENTOR(S) : Banholzer et al.

It is certified that error appears in the above-identified patent and that said Letters Patent is hereby corrected as shown below:

In Column 10, line 4 (Claim 22):
"A method for treatment of diseases in which the administration...." should read
--A method for treatment of the diseases asthma or COPD in which the administration....--

In Column 10, line 15 (Claim 23):
"A method for treatment of diseases in which the administration...." should read
--A method for treatment of the diseases asthma or COPD in which the administration....--

In Column 10, line 22 (Claim 23):
"K/mm" should read
--K/min--

Signed and Sealed this

Fifth Day of May, 2009

JOHN DOLL
*Acting Director of the United States Patent and Trademark Office*